(12) United States Patent  (10) Patent No.: US 8,409,522 B2
Kitamura  (45) Date of Patent: Apr. 2, 2013

(54) ANALYZING INSTRUMENT, TEMPERATURE CONTROL METHOD FOR LIQUID IN ANALYZING INSTRUMENT, AND ANALYZING APPARATUS

(75) Inventor: Shigeru Kitamura, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 909 days.

(21) Appl. No.: 12/537,080

(22) Filed: Aug. 6, 2009

(65) Prior Publication Data

US 2009/0297402 A1 Dec. 3, 2009

Related U.S. Application Data

(62) Division of application No. 10/532,871, filed as application No. PCT/JP03/13670 on Oct. 24, 2003, now abandoned.

(30) Foreign Application Priority Data

Oct. 28, 2002 (JP) ................................. 2002-312963

(51) Int. Cl.
*G01N 21/75* (2006.01)
*G05D 23/00* (2006.01)

(52) U.S. Cl. ........ 422/400; 422/402; 422/403; 422/417; 422/426; 422/68.1; 422/502; 422/108; 422/109; 422/186; 422/186.01

(58) Field of Classification Search .............. 422/400, 422/417, 425–426, 429, 68.1, 82.05, 500, 422/502, 547, 551, 554, 109, 186, 186.01, 422/402–403, 108
See application file for complete search history.

(56) References Cited

U.S. PATENT DOCUMENTS

| | | | |
|---|---|---|---|
| 4,904,336 A | 2/1990 | Ozawa et al. | |
| 5,035,862 A | 7/1991 | Dietze et al. | |
| 5,073,625 A | 12/1991 | Derbyshire | |
| 5,108,701 A | 4/1992 | Zakaria et al. | |
| 5,110,727 A * | 5/1992 | Oberhardt | 435/13 |
| 5,240,674 A | 8/1993 | Armor | |
| 5,318,754 A | 6/1994 | Collins et al. | |
| 5,443,795 A | 8/1995 | Revesz | |
| 5,599,502 A | 2/1997 | Miyazaki et al. | |
| 5,681,529 A | 10/1997 | Taguchi et al. | |
| 5,858,303 A | 1/1999 | Schiffmann et al. | |
| 5,997,708 A * | 12/1999 | Craig | 204/601 |
| 6,036,922 A | 3/2000 | Kawamura et al. | |
| 6,207,462 B1 | 3/2001 | Barclay et al. | |
| 6,482,638 B1 | 11/2002 | Patil et al. | |
| 6,536,477 B1 * | 3/2003 | O'Connor et al. | 137/833 |
| 6,555,389 B1 | 4/2003 | Ullman et al. | |
| 6,593,143 B1 | 7/2003 | Gordon | |
| 6,607,662 B1 | 8/2003 | Ikeda et al. | |
| 6,610,978 B2 * | 8/2003 | Yin et al. | 250/288 |
| 6,756,223 B2 | 6/2004 | Roberts et al. | |

(Continued)

FOREIGN PATENT DOCUMENTS

EP 1 010 979 6/2000
JP 4-243548 8/1992

(Continued)

*Primary Examiner* — Brian R Gordon
(74) *Attorney, Agent, or Firm* — Fox Rothschild LLP

(57) ABSTRACT

This invention relates to a technique for adjusting the temperature of a liquid held on an analyzing instrument (1) to a target value. The invention provides a temperature control method wherein thermal energy is supplied to liquid (10) by passing a magnetic flux across an analyzing instrument (1) for raising the temperature of the liquid. The invention also provides an analyzing instrument (1) and analyzing apparatus (X) which are suited to raising the temperature of a liquid (10) using a magnetic flux.

4 Claims, 8 Drawing Sheets

U.S. PATENT DOCUMENTS

| | | | |
|---|---|---|---|
| 6,761,962 B2 * | 7/2004 | Bentsen et al. | 428/188 |
| 7,192,559 B2 * | 3/2007 | Chow et al. | 422/504 |
| 7,364,896 B2 * | 4/2008 | Schembri | 435/287.1 |
| 2002/0085967 A1 | 7/2002 | Yokota | |
| 2003/0027352 A1 * | 2/2003 | Hooper et al. | 436/169 |
| 2005/0170490 A1 * | 8/2005 | Chen et al. | 435/287.1 |

FOREIGN PATENT DOCUMENTS

| | | |
|---|---|---|
| JP | 6-10900 | 1/1994 |
| JP | 8-114539 | 5/1996 |
| JP | 9-110730 | 4/1997 |
| JP | 9-189703 | 7/1997 |
| JP | 9-304269 | 11/1997 |
| JP | 9-329589 | 12/1997 |
| JP | 10-253536 | 9/1998 |
| JP | 2001-340753 | 12/2001 |
| JP | 2002-090357 | 3/2002 |
| WO | WO 01/07890 | 2/2001 |

* cited by examiner

ANALYZING INSTRUMENT, TEMPERATURE CONTROL METHOD FOR LIQUID IN ANALYZING INSTRUMENT, AND ANALYZING APPARATUS

This application is a division of U.S. Ser. No. 10/532,871, filed Apr. 27, 2005, now abandoned, is a U.S. National Stage application of International No. PCT/JP2003/013670 filed 24 Oct. 2003, which application is incorporated herein by reference.

TECHNICAL FIELD

The present invention relates to a technique for adjusting the temperature of a liquid held on an analyzing instrument to a target value, in analysis of a sample with use of the analyzing instrument.

BACKGROUND ART

Methods of analyzing a sample include methods in which the reaction liquid resulting from the reaction of a sample and a reagent is analyzed by optical means. Such analysis is accomplished for example by mounting an analyzing instrument which provides a reaction field on an analyzing apparatus equipped with an optical system capable of emitting and receiving light (see for example JP-A 8-114539). In this case, it is desirable to adjust the temperature of the analyzing instrument (particularly the reaction liquid), and to react the sample and reaction liquid at roughly the same temperature for each measurement so as to minimize analysis error and increase the reliability of the analysis results. In systems using enzyme reactions in particular, because the reaction speed is highly temperature-dependent the temperature of the system is preferably adjusted to within ±0.1° C. of the target temperature.

Methods of adjusting the temperature of a reaction liquid include for example the method illustrated in FIG. 9A in which analyzing instrument 9 is held on heat block 91, which had a greater heat capacity than reaction liquid 90, and the temperature of reaction liquid 90 is adjusted by controlling the temperature of this heat block 91 (see for example JP-A 9-189703 and JP-A 10-253536). In this method, the temperature of reaction liquid 90 is monitored by means of temperature sensor 92 embedded in heat block 91 for example, and when the temperature of reaction liquid 90 falls below a specified value, heat block 91 is heated to raise its temperature, thus raising the temperature of reaction liquid 90 via heat block 91. Moreover, as shown in FIG. 9B there is another method in which analyzing instrument 9 is held on heat generator 93, which has high temperature continuity, and the temperature of reaction liquid 90 is directly adjusted by means of this heat generator 93 (see for example JP-A 9-304269). In this method as well, heat generator 93 is driven in accordance with the monitoring results from temperature sensor 92 to control the temperature of reaction liquid 90.

These temperature control methods have the drawback of high energy consumption because it is necessary to heat block 91 or drive heat generator 93 when raising the temperature of reaction liquid 90. Moreover, with heating media such as heat block 91 and heat generator 93, it is difficult to exactly heat only that region where reaction liquid 90 is held when the amount of reaction liquid 90 is small as in a microdevice. Consequently, heating media 91 and 93 need to be relatively large in comparison with the region that needs to be heated (the region directly below reaction liquid 90 in the figure) in order to raise the temperature of reaction liquid 90 with good responsiveness. As a result, when controlling the temperature of a reaction liquid in microdevice energy efficiency is poor because the amount of heat used for raising the temperature of reaction liquid 90 is small in comparison with the amount of heat transmitted by heating media 91 and 93.

Thus, conventional temperature control methods have had the drawback of high energy consumption. Consequently, it has been difficult to apply conventional temperature control methods to analyzing apparatuses driven by internal power sources such as small batteries (for example, batteries widely used for household use), and even if the aforementioned methods were applied to a small analyzing apparatus it would not be practical because the actual working time of the analyzing apparatus would be extremely short. And while the shortness of the actual working time can be improved by increasing the capacity of the internal power source, this impedes miniaturization of the analyzing apparatus and detracts from wide use. Power can also be supplied from an external source, but in that case an adapter is necessary to connect the analyzing apparatus to the external power source, making it less portable and also creating problems for use in other locations.

DISCLOSURE OF THE INVENTION

It is an object of the present invention to allow a liquid held in an analyzing instrument to be adjusted to a target temperature with low energy consumption and without making the analyzing apparatus large.

According to a first aspect of the present invention, a method is provided for controlling the temperature of a liquid held on an analyzing instrument to a target value, wherein thermal energy is supplied to the liquid by the passing a magnetic flux across the analyzing instrument for raising the temperature of the liquid.

According to a second aspect of the present invention, an analyzing instrument is provided which is an analyzing instrument to be used in analyzing a sample. The analyzing instrument comprises a heating layer which heats up when magnetic flux is passed through it.

When using the analyzing instrument, the temperature of the liquid is raised using the thermal energy from the heating layer which has been heated.

The heating layer is formed for example as a thin metal film. Materials which can be used for forming the thin metal film include typically aluminum, nickel, copper, iron and stainless steel for example. When forming the thin metal film using a material (such as aluminum, nickel or copper) with low resistance, the thin metal film is preferably formed to a thickness of 1-200 μm for example. This is because if the thin metal film is unsuitably thick the resistance of the thin metal film will be reduced and it will be impossible to generate sufficient thermal energy in the thin metal film, while if the thin metal film is unsuitably thin the resistance of the thin metal film will be greater and it will melt, making it difficult to supply the target thermal energy to the liquid.

The heating layer can also be formed from a conductive resin material. Conductive resin materials which can be used include for example either insulating resins in which conductive fillers have been dispersed to make them conductive and conductive polymers which are intrinsically conductive. Examples of conductive polymers include polyacetylene, polypyrrole, polythiophene, polyaniline, polyisothianaphthene, polyazulene, poly-P-phenylene, poly-P-phenylenevinylene, poly-2,5-thienylenevinylene and polyperinaphthalene. As in the case of a thin metal film, when the heating layer is formed from a conductive polymer material the thickness of the heating layer is set within a range at which it can appropriately provide thermal energy to the liquid.

The heating layer is formed either by direct film formation on a constituent element of the analyzing instrument, or by working the material into a sheet which is affixed to or fit into an indentation in the aforementioned constituent element. Methods of forming the heating layer as a film include vapor deposition, sputtering and CVD for example. These methods are useful when aluminum, nickel or copper is used as the metal material.

The analyzing instrument of the present invention can be made to comprise a reaction zone for reacting a sample and a reagent for example. In this case at least the liquid present in the reaction zone should be heated. In the analyzing instrument the heating layer is preferably formed in a location where it can supply thermal energy to the liquid in the reaction zone. More specifically, the heating layer is formed in a location covering the periphery of the reaction zone, a location covering the reaction zone or a location inside the reaction zone.

In the present invention the temperature of the liquid can be controlled by monitoring the temperature of the liquid and using the monitoring results as feedback for repeatedly controlling the state of magnetic flux passed through the analyzing instrument. The temperature of the liquid can also be controlled by first ascertaining the relationship between the environmental temperature around the liquid and the passage state of magnetic flux in the analyzing instrument necessary for raising the liquid to the target temperature, determining the amount of control necessary to achieve the target state of the magnetic flux based on the aforementioned relationship and the measured environmental temperature, and then controlling the state of the magnetic flux in the analyzing instrument according to this amount of control.

According to a third aspect of the present invention, a temperature detecting analyzing apparatus is provided for analyzing a sample with use of a sample-holding analyzing instrument while adjusting a temperature of a liquid held on the analyzing instrument. The analyzing apparatus comprises a magnetic generating coil for generating a magnetic flux across the analyzing instrument.

Desirably, the analyzing apparatus of the present invention may also comprise a temperature detector for measuring the temperature of the liquid or the environmental temperature around the liquid, and a controller for controlling the generation of magnetic flux in the magnetic generating coil based on the measurement results of the temperature detector.

The analyzing apparatus may further comprise for example with An AC voltage applier for causing the magnetic generating coil to generate a magnetic flux. In this case, the controller controls the generation of the magnetic flux in the magnetic generating coil by controlling the an AC voltage applier. More specifically, the controller controls the strength of the magnetic flux (effective value of AC voltage), the frequency (frequency of applied voltage) of repetitively altering the direction of the magnetic flux, and the time for passing the magnetic flux (time for applying the AC voltage). In this way, the generation of magnetic flux in the magnetic generating coil and hence the amount of heat generated when the magnetic flux is passed through the analyzing instrument is controlled, and ultimately it is possible to control the amount of thermal energy which should be transmitted to the liquid.

The present invention can be applied to controlling the temperature of a liquid in a microdevice for analyzing a tiny sample quantity. "Tiny sample quantity" here signifies a sample of 100 μL or less.

It should be pointed out that the term "liquid" as used in the present invention refers to a portion of liquids held in the analyzing instrument which is subject to temperature control, which in the absence of special limitations may be all of the liquids on the analyzing instrument or part of those liquids. For example, in a system for reacting a liquid sample with a liquid reagent, it may signify either the liquid sample, the liquid reagent or the reaction liquid of these, or it may signify more than one of these, or in the case of a reaction liquid it may signify a portion of the reaction liquid present in a specific region.

BEST MODE FOR CARRYING OUT THE INVENTION

Embodiments 1 through 5 of the present invention are explained below with reference to FIGS. 1 through 8.

First, the first embodiment of the present invention is explained with reference to FIGS. 1 through 3.

Figure 1:
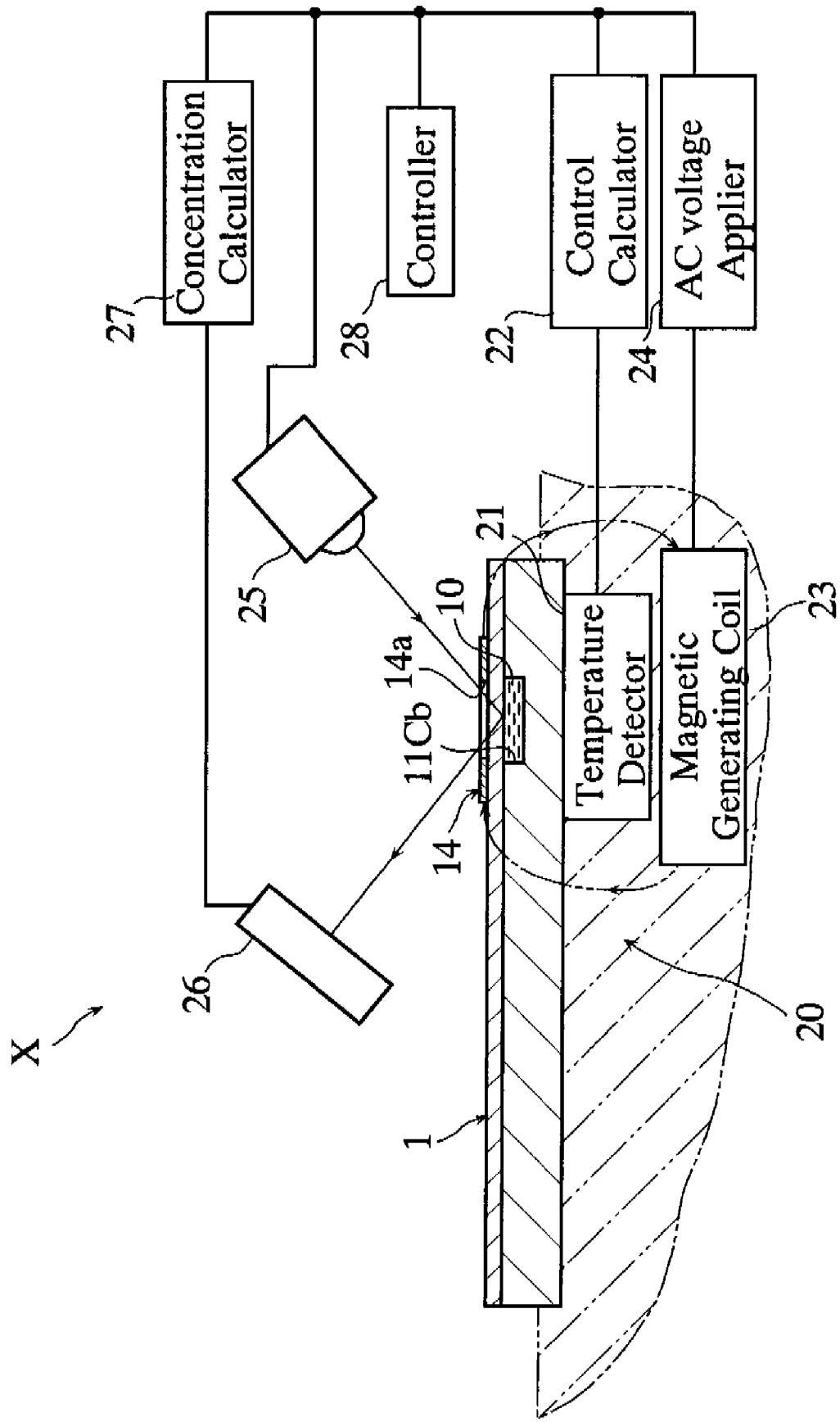
FIG. 1 is a typical view showing a simplified construction of one example of an analyzing apparatus of the present invention.

The analyzing apparatus X shown in FIG. 1 has an analyzing function for analyzing a sample using analyzing instrument 1, and a temperature control function for controlling the temperature of a liquid 10 held on measurement site 11Cb of analyzing instrument 1. To exercise these functions, analyzing apparatus X includes mount 20, temperature detector 21, control calculator 22, magnetic generating coil 23, AC voltage applier 24, light source 25, light detector 26, concentration calculator 27 and controller 28.

Mount 20 is for holding analyzing instrument 1. Temperature detector 21 is embedded in mount 20. This temperature detector 21 is arranged so as to be in a region directly underneath liquid 10 (measurement site 11Cb) held on analyzing instrument 1 when analyzing instrument 1 is mounted on mount 20. This means that the temperature measured by temperature detector 21 is closer to the actual temperature of liquid 10. A thermistor or thermocouple can be used as temperature detector 21. Of course, a non-contact type thermometer such as a radiation thermometer may also be used.

Control calculator 22 computes the amount of energy to be applied to liquid 10 based on the temperature measurement results of temperature detector 21, and calculates the amount of control for AC voltage applier 24.

Magnetic generating coil 23 is for generating a magnetic flux to pass through analyzing instrument 1. AC voltage applier 24 is for applying voltage to magnetic generating coil 23. An AC voltage applier 24 capable of applying AC voltage of a frequency selected from the range of 40-200 kHz for example can be used. In magnetic generating coil 23, a magnetic flux is generated in response to voltage applied by AC voltage applier 24. The state of the magnetic flux generated by magnetic generating coil 23 can be controlled by means of the voltage applied to magnetic generating coil 23. More specifically, the generation of the magnetic flux by magnetic generating coil 23 can be controlled by controlling the effective value of AC voltage applied to magnetic generating coil 23, the frequency of the applied voltage and the application times of AC voltage.

Light source 25 is for illuminating liquid 10 (measurement site 11Cb) with light, while light detector 26 is for receiving reflected light from liquid 10. Light source 25 is comprised for example by a mercury lamp or white LED. When these light sources are used, the light from light source 25 passes through a filter before illuminating liquid 10. This is done in order to select with the filter light of a wavelength matched to the light-absorption characteristics of the components to be analyzed in liquid 10. Light detector 26 is comprised for example by a photo diode.

Concentration calculator 27 is for computing the concentration of the sample liquid based on the results for light received at light detector 26. Concentration is computed for example by calculating reflectance based on results for liquid received by light detector 26 for example, and comparing it against reflectance previously computed on a calibration curve showing the relationship between reflectance and concentration.

Controller 28 is for controlling AC voltage applier 24 based on the amount of control computed by control calculator 22, and for controlling the generation of magnetic flux by magnetic generating coil 23. Controller 28 also selects whether light source 25 is lit or unlit, and controls the operations of control calculator 22 and concentration calculator 27.

Control calculator 22, concentration calculator 27 and controller 28 can be comprised for example by a CPU, ROM and RAM, and in this case the program recorded in ROM is executed by the CPU using RAM in order to control AC voltage applier 24 and control the generation of magnetic flux by magnetic generating coil 23.

Figure 2:
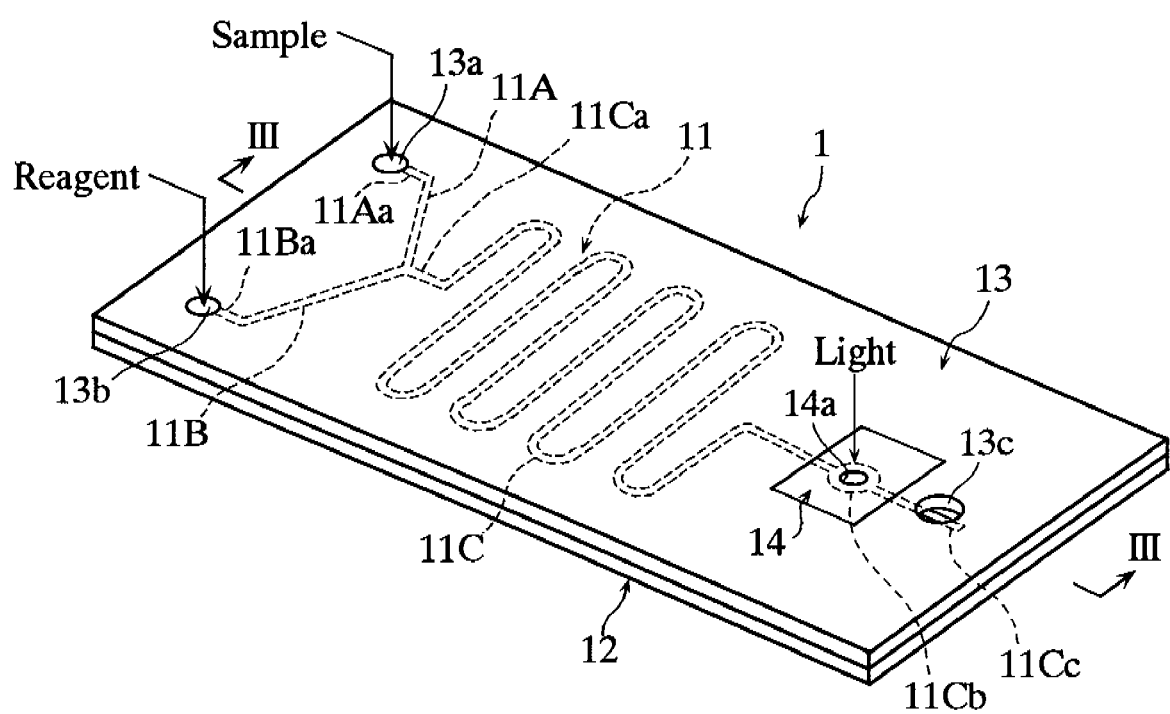
FIG. 2 is a complete oblique view of one example of a microdevice according to the present invention.
Figure 3:
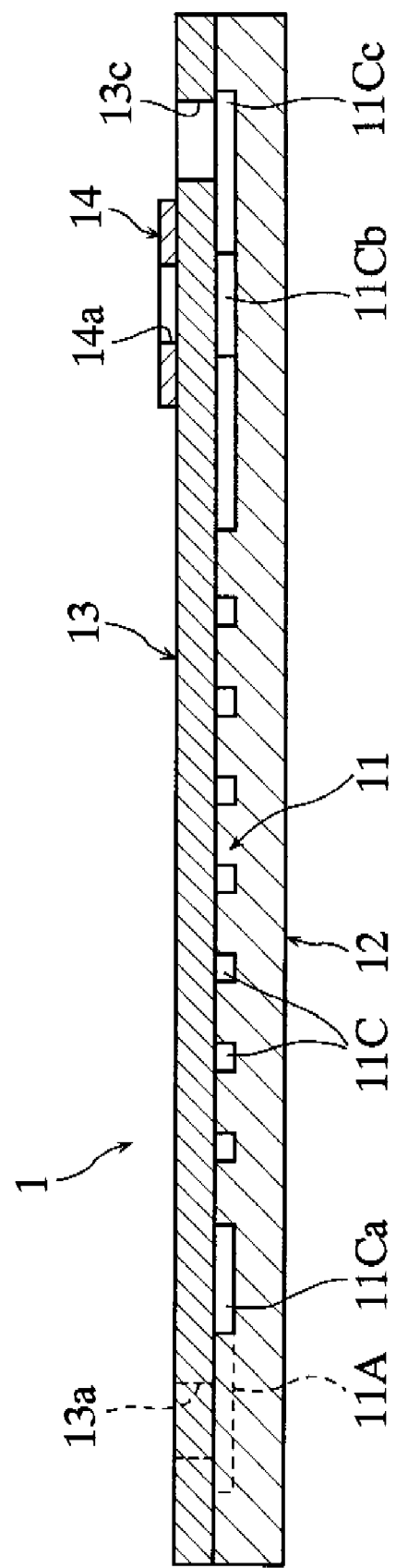
FIG. 3 is a cross-section along line III-III in FIG. 2.

An analyzing instrument 1 such as that shown in FIGS. 2 and 3 for example can be used. The analyzing instrument 1 shown in these figures is designed as a so-called microdevice. This analyzing instrument 1 provides a reaction field and is formed with cover 13 laid so as to cover channel 11, which is formed on substrate 12.

Channel 11 has sample inlet 11A, reagent inlet 11B and reaction channel 11C. Sample inlet 11A and reagent inlet 11B are connected to end 11Ca of reaction channel 11C. Reaction channel 11C is arranged in accordion folds so as to increase the length of the channel. Reaction channel 11C is provided with measurement site 11Cb (see FIG. 1) which is exposed to light from light source 25.

Correspondingly, cover 13 has sample inlet 13a, reagent inlet 13b and air vent 13c. Sample inlet 13a, reagent inlet 13b and air vent 13c are formed at sites corresponding to end 11Aa of sample inlet 11A, end 11Ba of reagent inlet 11B and end 11Cc of reaction channel 11C, respectively. Heating layer 14 is formed in cover 13.

Heating layer 14 is heated by induction current resulting from the passage of magnetic flux generated by magnetic generating coil 23 (see FIG. 1), and has through hole 14a. Through hole 14a is for allowing measurement site 11Cb to be illuminated with light from light source 25 (see FIG. 1) and for allowing reflected light from measurement site 11Cb to be received by light detector 26 (see FIG. 1). Thus, heating layer 14 is provided directly above measurement site 11Cb so as to cover the margin and periphery of measurement site 11Cb. In such an arrangement of heating layer 14 the heat energy generated in heating layer 14 can be efficiently transmitted to liquid component 10 of measurement site 11Cb.

So as to function effectively, heating layer 14 is formed as a film with a thickness of 1-200 μm by a method such as vapor deposition, sputtering or plating of aluminum, nickel or copper for example. Heating layer 14 can also be formed by affixing a sheet formed from metal material to the surface of cover 13. The metal material used in this case can by iron or stainless steel in addition to aluminum, nickel and copper for example. Heating layer 14 can also be formed from a conductive resin material.

The analyzing instrument 1 shown in FIGS. 2 and 3 may be one which mixes and reacts two liquids, a sample and a reagent, but one which mixes three or more liquids can also be used as a microdevice, as can one having multiple channels formed so as to construct multiple reaction system.

When analyzing a sample, the sample is introduced into analyzing instrument 1 through sample inlet 13a and reagent through reagent inlet 13b. This sample and reagent move through sample inlet 11A and reagent inlet 11B by capillary action, converging at reaction channel 11C. In this way, the sample and reagent begin to react. The sample and reagent continue to react as they move through reaction channel 11C towards air vent 13c by capillary action, finally arriving at measurement site 11Cb.

During this time, the temperature of the reaction liquid (liquid 10) arriving at measurement site 11Cb is measured continuously by the temperature detector 21 shown in FIG. 1. These measurement results are sent to control calculator 22 and form the basis for computing control.

This control calculator 22 compares the target temperature of liquid 10 with the actual measured temperature, and when the measured temperature is lower than the target temperature it computes the control for AC voltage applier 24. Computation of control is performed by entering the measured temperature (or difference between target temperature and measured temperature) into a previous determined formula. The computation results are sent to controller 28.

In response, controller 28 controls AC voltage applier 24 according to the computation results from control calculator 22, thus controlling generation of magnetic flux by magnetic generating coil 23. In this way, a magnetic flux is passed across heating layer 14, causing heating layer 14 to heat up and raise the temperature of liquid 10 by thermal energy just by the difference between the measured temperature and the target temperature. On the other hand, if the measured temperature is higher than the target temperature, controller 28 controls AC voltage applier 24 so that voltage is not applied to magnetic generating coil 23. This control of AC voltage applier 24 and hence control of the generation of magnetic flux by magnetic generating coil 23 is performed repeatedly based on feedback of measurement results from temperature detector 21, so that the temperature of liquid 10 is kept roughly constant.

Temperature control of liquid 10 can also be accomplished based on the environmental temperature which is measured around liquid 10. More specifically, the relationship between the environmental temperature and the amount of control of magnetic generating coil 23 (AC voltage applier 24) needed to raise liquid 10 to a target temperature is ascertained in advance. This relationship is made into a table and recorded on control calculator 22 and the like. The amount of control (control of AC voltage applier 24) needed to achieve the target passage state of the magnetic flux is determined based on the measured environmental temperature and the aforementioned relationship, and the passage of the magnetic flux through heating layer 14 is controlled according to this amount of control. In this method, control can be exercised once rather than AC voltage applier 24 being controlled repeatedly using the measured environmental temperature results for example as feedback.

As explained above, in this embodiment the temperature of liquid 10 is raised using thermal energy which occurs when induced current is generated in heating layer 14. Consequently, in the present invention the usage efficiency of supplied energy is improved because concentrated heating of liquid 10 is possible. Moreover, thermal energy can be transmitted efficiently from heating layer 14 to liquid 10 because heating layer 14 can be placed close to liquid 10. This also means an improvement in the usage efficiency of supplied energy. Consequently, in the present invention it is possible to reduce the power consumption required for temperature control. As a result, even if AC voltage applier 24 is constructed with a small battery as its internal power source, it will be possible to adequately raise the temperature of liquid 10 without dramatically reducing battery life. Consequently, temperature control of liquid 10 can be accomplished using a small battery in a small analyzing apparatus X without enlarging the apparatus. Moreover, if this can be accomplished with an internal power source there is no need to attach an external power source, and no adapter is required. Portability is therefore good because there is no need to carry an adapter when carrying analyzing instrument X.

Of course, the present invention is not limited by the embodiments above and various design changes are possible. For example, in this embodiment an example was given of an analyzing instrument designed to perform analysis based on reflected light when a liquid is exposed to light, but the present invention is also applicable to an analyzing tool and analyzing apparatus designed to analyze a liquid based on transmitted light. Moreover, temperature control may be applied not only to with respect to the liquid at measurement site 11Cb but also or alternatively to a liquid present in at least one of sample inlet 11A, reagent inlet 11B and reaction channel 11C (other than measurement site 11Cb).

Figure 4A:
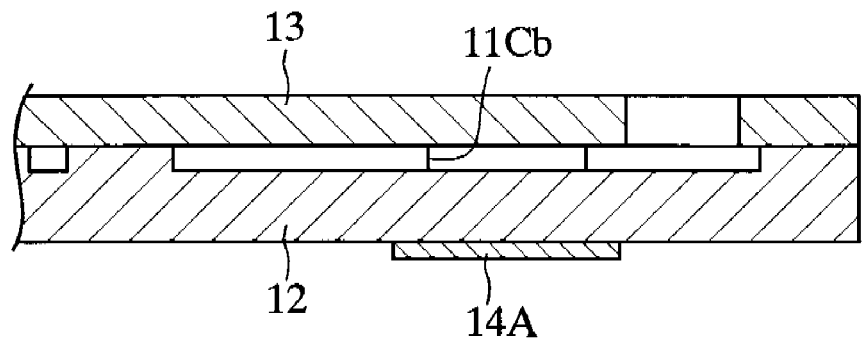
FIGS. 4A through 4D are component cross-sections showing other examples of installation sites for the heating layer.
Figure 4B:
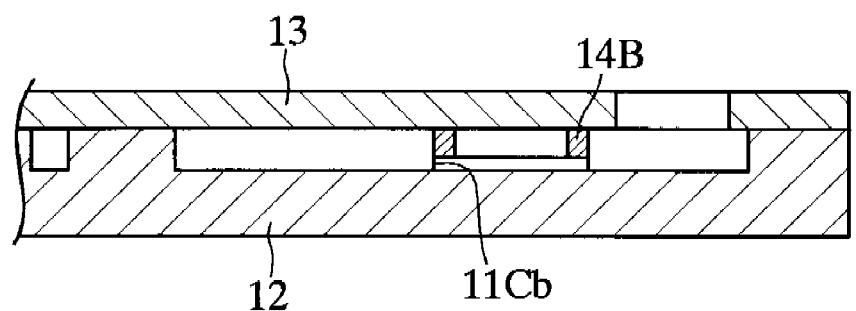
Figure 4C:
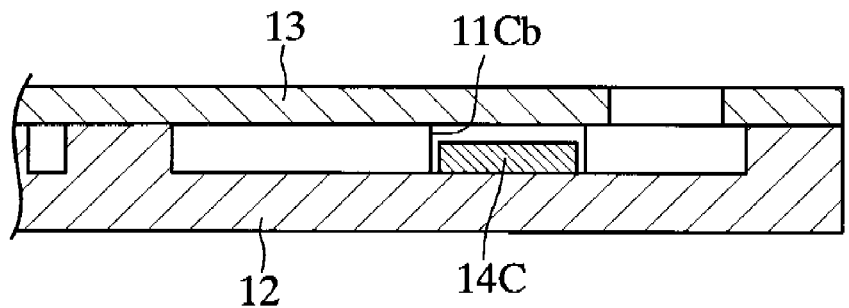
Figure 4D:
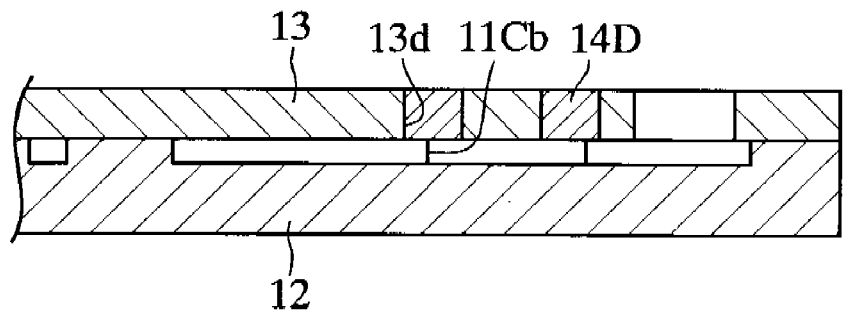

In the analyzing instrument 1 shown in FIGS. 1 through 3, heating layer 14 is provided on the top surface of cover 13 so as to be directly above measurement site 11Cb (liquid), but as shown in FIG. 4A heating layer 14A may also be provided on the bottom surface of substrate 12 so as to be directly underneath measurement site 11Cb (liquid). Heating layer 14B can also be located facing measurement site 11Cb on the underside of cover 13 as shown in FIG. 4B, or heating layer 14C can be provided at the bottom of measurement site 11Cb on substrate 12 as shown in FIG. 4C, or heating layer 14D can be embedded in through hole 13d formed in cover 13 as shown in FIG. 4D. Moreover, cover 13 can be formed of a conductor or resister so that cover 13 itself functions as a heating body.

The magnetic generating coil is not limited need not be positioned underneath analyzing apparatus 1 as shown in FIG. 1, and other positions are possible. For example, magnetic generating coil 23 may be positioned above analyzing instrument 1. Moreover, the heating layer 14 provided in analyzing instrument 1 may also be provided in analyzing apparatus X on mount 20 for example.

Next, the second embodiment of the present invention is explained with reference to FIG. 5.

Figure 5:
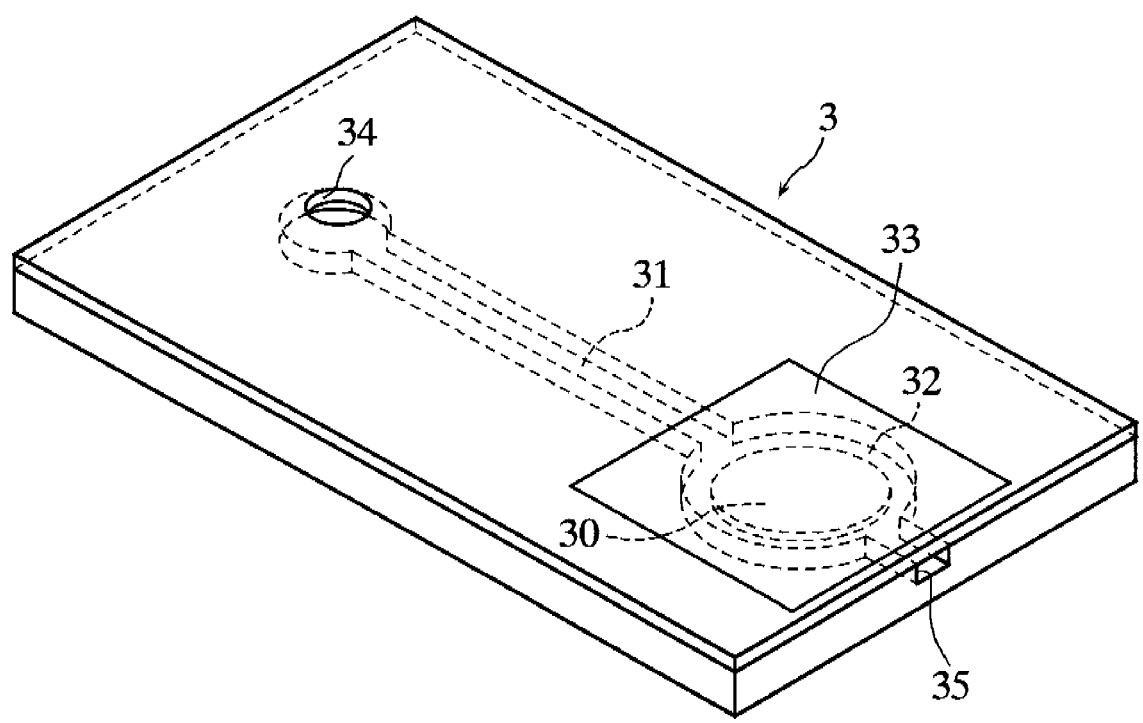
FIG. 5 is a complete oblique view of an analyzing instrument according to the second embodiment.

In the analyzing instrument 3 shown in FIG. 5 reagent is not supplied to analyzing instrument 3 from the outside, and instead analyzing instrument 3 already holds reagent in reagent part 30.

In analyzing instrument 3 measurement site 32 is provided partway along channel 31, reagent part 30 is held in this measurement site 32, and heating layer 33 is provided directly above measurement site 32. This analyzing instrument 3 is designed so that sample introduced from sample inlet 34 moves by capillary action towards air vent 35, and is supplied to measurement site 32.

In measurement site 32 reagent 30 is dissolved by the supply of sample to construct a liquid reaction system. Thermal energy generated in heating layer 33 by the passage of magnetic lines of force through heating layer 33 can be supplied to the liquid (liquid phase reaction system) held in this measurement site 32.

Next, the third and fourth embodiments of the present invention are explained with reference to FIGS. 6A and 6B.

Figure 6A:
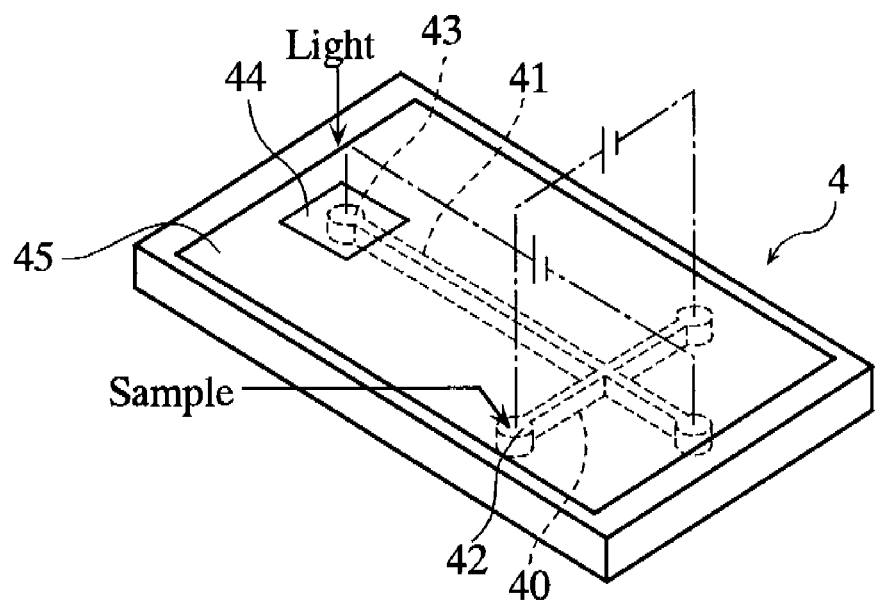
FIGS. 6A and 6B are complete oblique views of analyzing instruments according to the third and fourth embodiments.

The analyzing instrument 4 shown in FIG. 6A is constructed so as to move sample and reagent by electrophoresis. In this analyzing instrument 4, the two channels 40 and 41 intersect each other, and film 45 is affixed so as to cover these channels 40 and 41.

Channels 40 and 41 are both filled with migration buffer, and during analysis potential difference is applied to both ends of channels 40 and 41 so that sample introduced through inlet 42 moves through channel 41 towards measurement site 43 while reacting in channel 41.

Heating layer 44 is provided directly above measurement site 43. In this analyzing instrument 4, the temperature of the liquid held in measurement site 43 can be raised by heating layer 44 using magnetic flux.

Figure 6B:
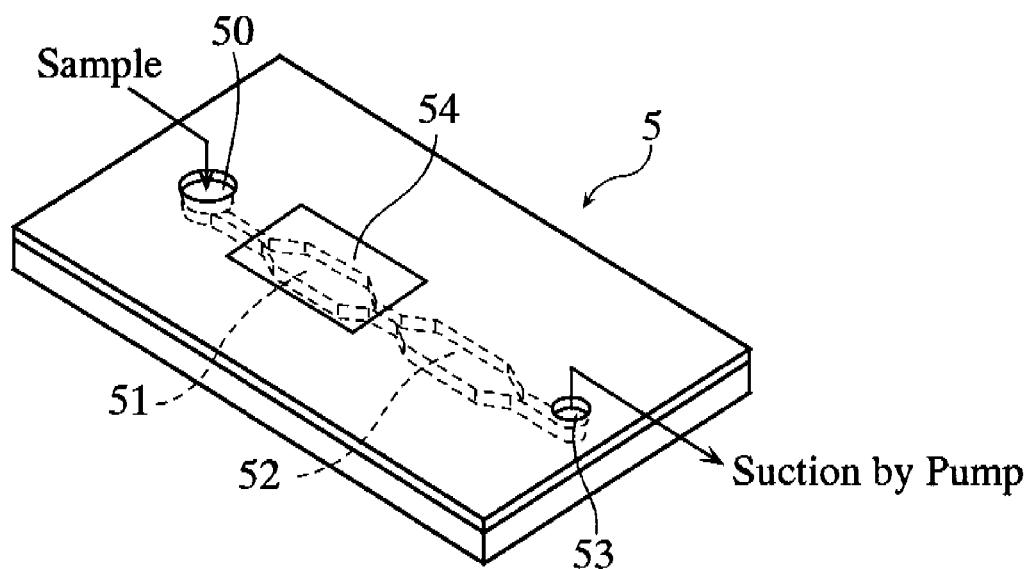

The analyzing instrument 5 shown in FIG. 6B is constructed so that sample is moved by means of the power of an external pump. In this analyzing instrument 5, sample inlet 50, reaction zone (measurement site) 51, waste reservoir 52 and suction part 53 are formed in a line. Heating part 54 is provided so as to be directly above reaction zone (measurement site) 51.

In this analyzing instrument 5, suction part 53 is connected to an external pump, and sample is moved by the power of the pump. Of course, it could also be an analyzing instrument constructed so as to move sample and the like by means of an internal micropump using a piezoelectric element.

In the analyzing instruments 4 and 5 shown in FIGS. 6A and 6B, heating elements 44 and 54 can be formed not only directly over measurement sites 43 and 51 but also covering all of the part which holds the liquid, so as to control the temperature of all liquids.

Next, an analyzing instrument according to the fourth embodiment of the present invention is explained with reference to FIGS. 7 and 8.

Figure 7:
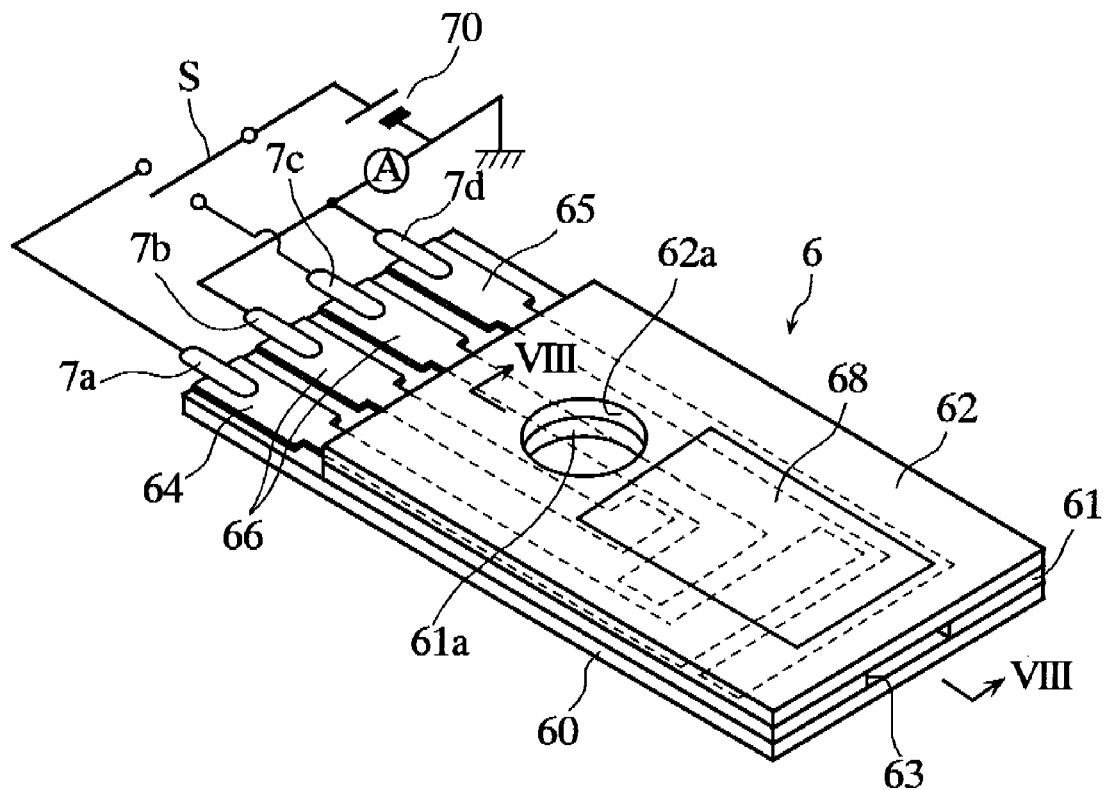
FIG. 7 is a complete oblique view of an analyzing instrument according to the fifth embodiment.
Figure 8:
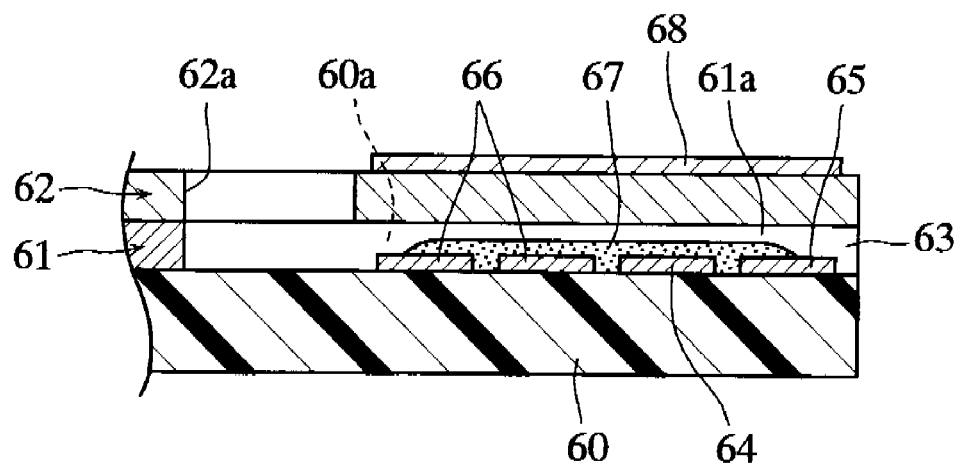
FIG. 8 is a cross-section along line VIII-VIII in FIG. 7.
Figure 9A:
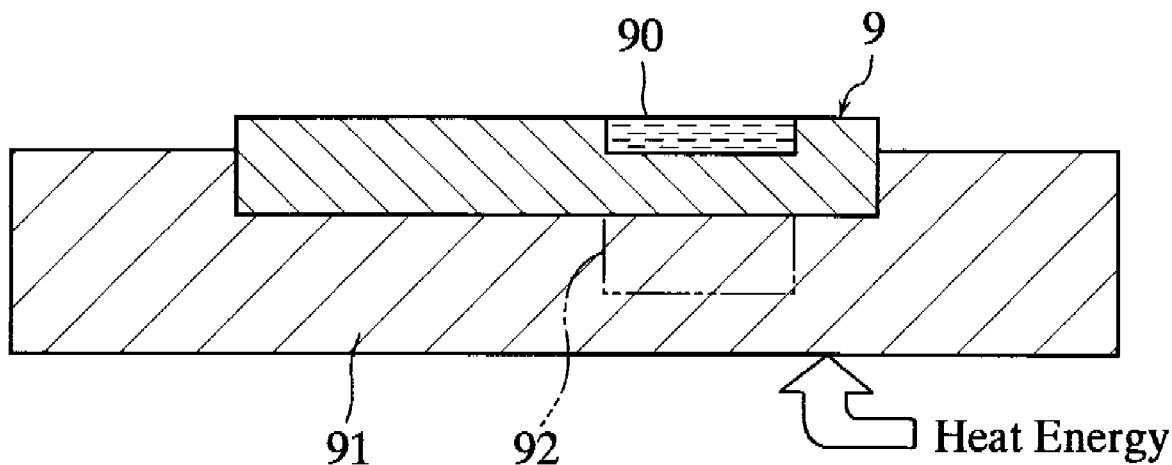
FIGS. 9A and 9B are cross-sections showing the necessary parts of an analyzing apparatus for explaining conventional temperature control methods.
Figure 9B:
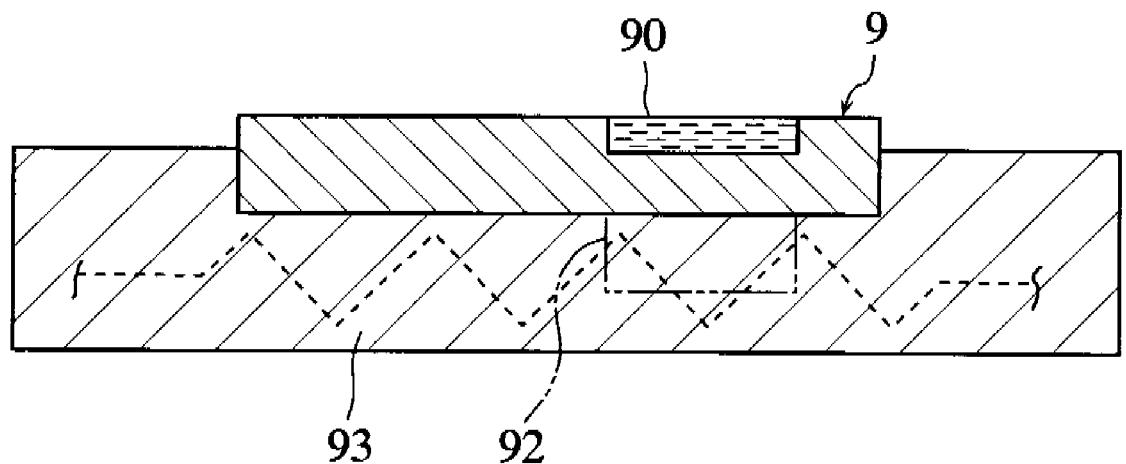

The analyzing instrument 6 shown in FIGS. 7 and 8 is constructed so as to analyze a sample by electrochemical means. This analyzing instrument 6 is provided with capillary 60a on substrate 60. Capillary 60a is formed by laying cover 62 in which is formed opening 62a over substrate 60 with spacer 61 having slit 61a in between. Heating layer 68 is provided in this cover 62 so as to be directly above capillary 60a. Sample liquid inlet 63 is set at the end of capillary 60a, within which is held reagent 67 in solid form. Sample liquid introduced from sample liquid inlet 63 dissolves reagent 67 as it moves through capillary 60a towards opening 62a by capillary action.

Working electrode 64 which is the measurement electrode is provided on substrate 60 along with counter electrode 65 and a pair of detection electrodes 66. Correspondingly, the analyzing apparatus has measurement terminals 7a and 7b and detection terminals 7c and 7d for contacting electrodes 64 through 66. Terminals 7b and 7d are connected to a ground while terminals 7a and 7c can be connected to power source 70. By switching switch S, it is possible to select either a state in which power source 70 applies a potential difference between working electrode 64 and counter electrode 65, or one in which a potential difference is applied between the pair of detection electrodes 66.

In this analyzing instrument 6, voltage is applied to the reaction liquid of a sample and reagent 67 for example to achieve electron transfer between the reaction product and the electrodes, and the analyzing apparatus is constructed so as to measure response current corresponding to the amount of electron transfer.

The reaction system is also constructed in capillary 60a in this analyzing instrument 6, and the temperature of the reaction system can be raised and hence the temperature of the reaction system can be controlled by supplying the reaction system with thermal energy generated by the passage of magnetic flux through heating layer 68.

In analyzing instrument 6, because electrodes 64 through 66 are formed from conductors induction current can be produced for electrodes 64 through 66. Consequently, heating layer 68 can be omitted and the temperature of the liquid raised by passing magnetic flux through electrodes 64 through 66 to heat them.

Of course, the analyzing instrument 6 shown in FIGS. 7 and 8 and the corresponding analyzing apparatus are examples, and the present invention is applicable in other cases in which a sample is electrochemically analyzed using a different structure.

The invention claimed is:

1. A combination comprising an analyzing instrument and a temperature detecting analyzing apparatus;

the analyzing instrument comprising a substrate, a cover laminated over the substrate, a sample channel formed between the substrate and the cover for allowing flow of a sample liquid, a heating layer formed over the cover for heating a sample liquid in the sample channel to a target temperature, the sample channel including a measurement zone, the heating layer having a through-hole corresponding to the measurement zone; and the temperature detecting analyzing apparatus comprising a magnetic generating coil for electromagnetically generating heat in the heating layer, wherein the temperature detecting analyzing apparatus further comprises a mount for supporting the analyzing instrument, a temperature detector provided in the mount for detecting a temperature of the sample liquid or an environmental temperature, a voltage applier for supplying electric energy to the magnetics generating coil, a control calculator for calculating an amount of electrical energy needed for heating the sample liquid to the target temperature based on a detection result of the temperature detector, and a controller for causing the voltage applier to supply the calculated amount of electric energy to the magnetic generating coil.

2. The combination according to claim 1, wherein the heating layer is formed as a metal film.

3. The combination according to claim 2, wherein the metal film is formed of aluminum, nickel or copper to have a thickness of 1-200 μm.

4. The combination according to claim 1, wherein the analyzing apparatus further comprises a light source for directing light onto the measurement zone via the though-hole of the heating layer, and a light detector for detecting light reflected from the measurement zone.

* * * * *